United States Patent [19]

Turko et al.

[11] Patent Number: 4,815,659

[45] Date of Patent: Mar. 28, 1989

[54] METHOD FOR RELEASING A GAS INTO THE ATMOSPHERE

[75] Inventors: John W. Turko, River Rouge; Kenneth S. Czerwinski, Detroit, both of Mich.

[73] Assignee: Michigan Consolidated Gas Company, Detroit, Mich.

[21] Appl. No.: 97,798

[22] Filed: Sep. 16, 1987

[51] Int. Cl.[4] .................................................. A61L 9/12
[52] U.S. Cl. ........................................ 239/6; 206/0.7; 239/55; 239/58
[58] Field of Search ........................ 239/53, 54, 55, 56, 239/57, 58, 6; 206/0.7, 0.6, 0.5

[56] References Cited

U.S. PATENT DOCUMENTS

| | | | |
|---|---|---|---|
| 3,820,309 | 6/1974 | Cullen et al. | 206/0.5 |
| 3,961,040 | 6/1976 | Rabussier et al. | 239/53 |
| 4,014,501 | 3/1977 | Buckenmayer | 239/58 |
| 4,161,283 | 7/1979 | Hyman | 239/55 |
| 4,346,840 | 8/1982 | Gaiser et al. | 239/6 |
| 4,548,764 | 10/1985 | Munteanu et al. | 239/57 |
| 4,715,536 | 12/1987 | Capizzi et al. | 239/54 |

FOREIGN PATENT DOCUMENTS 0797760 1/1981 U.S.S.R. ............................... 206/0.7

Primary Examiner—Andres Kashnikow
Assistant Examiner—Christopher G. Trainor
Attorney, Agent, or Firm—Harness, Dickey & Pierce

[57] ABSTRACT

An apparatus for releasing gaseous material into the atmosphere employs a sorbent material that is sorptively saturated with a predetermined quantity of the gaseous material at a predetermined pressure, preferably approximately equal to atmospheric pressure. The gaseous material to be released preferably has a vapor pressure lower than the predetermined pressure at which the sorbent material is sorptively saturated. The apparatus also includes capability of selectively exposing the sorbent material to the atmosphere in order to allow the gaseous material to be desorptively released.

9 Claims, 1 Drawing Sheet

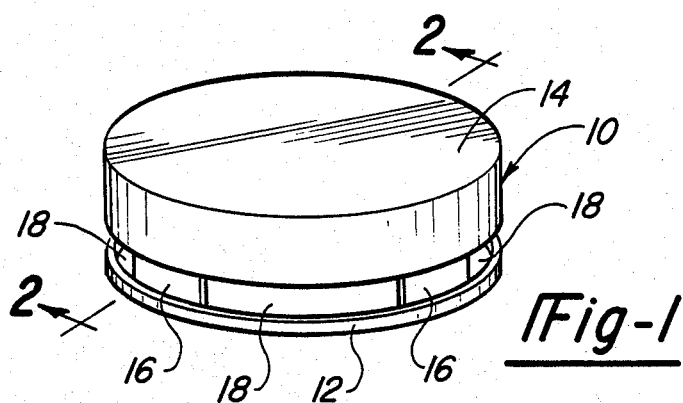
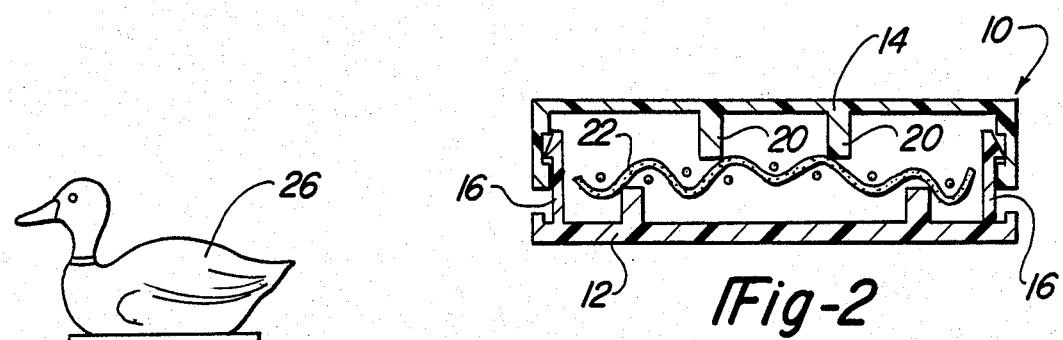
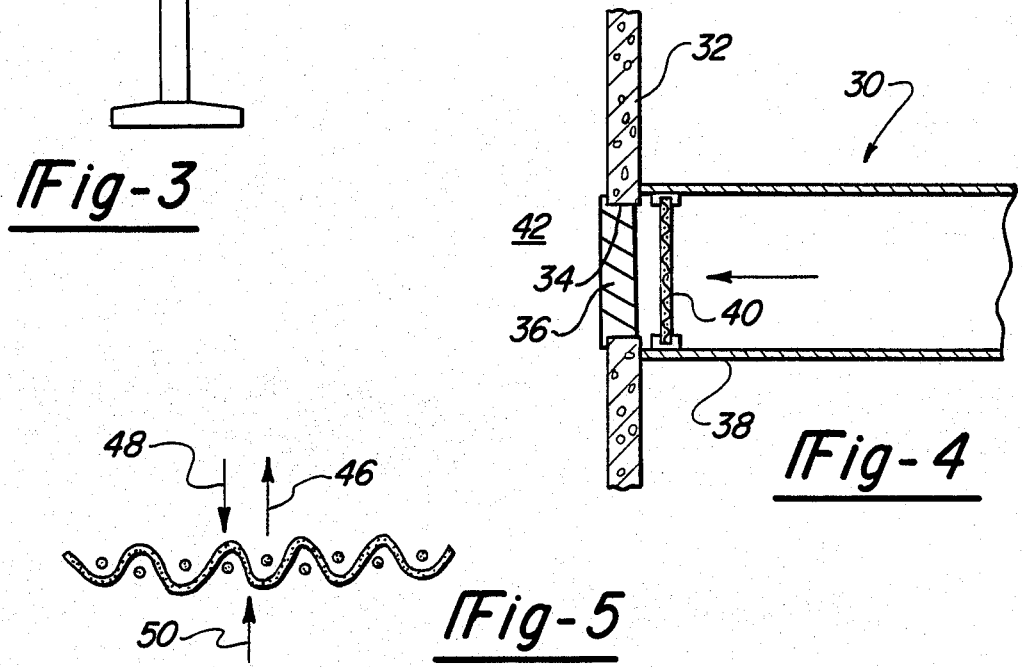

METHOD FOR RELEASING A GAS INTO THE ATMOSPHERE

BACKGROUND OF THE INVENTION

The invention relates generally to a method and apparatus for releasing a gaseous material into the atmosphere. More specifically, the invention relates to such a method and apparatus wherein a gaseous material is sorptively stored on a sorbent material, which is then selectively exposed to the atmosphere in order to cause such gas release. As used herein, the terms "sorbent" or "sorptive", or the like, refer to the use of either the use of an adsorbent or an absorbent.

Various devices have been provided for releasing a material, such as an odorant, an insect repellent, or an antiseptic or other medicinal substances into the atmosphere in order to create a pleasant odor, an insect-free region, or other beneficial atmospheric conditions. Typically such previous devices have included wicks or other such media onto which the material has been placed and allowed to be released into the atmosphere by an evaporation process. In other instances, the released material has been discharged into the atmosphere by a technique in which a water vapor released into the atmosphere serves as a carrier for the material. Typically, however, such previous devices have only been capable of storing a relatively small amount of the material to be released into the atmosphere, and thus have been relatively short-lived, requiring frequent replacement, maintenance, or recharging. In addition, such devices that use a released water vapor as a carrier for discharging the material into the atmosphere have required relatively expensive and complex vapor-producing mechanisms, which also require frequent maintenance and recharging with the material to be released.

In light of the above-discussed state-of-the-art, one of the object of the present invention is to provide an apparatus and method for releasing a gaseous material into the atmosphere in a predetermined, relatively controlled, concentration level, and which is capable of storing relatively large amounts of the released material in order to significantly lengthen the useful life of the apparatus. In addition, another object of the present invention is to provide such a method and apparatus that does not require the use of relatively expensive, complex, or high-maintenance mechanisms.

In accordance with the present invention, an apparatus for releasing gaseous material into the atmosphere employs a sorbent material that is sorptively saturated with a predetermined quantity of the gaseous material at a predetermined pressure, preferably approximately equal to atmosphere pressure. The gaseous material to be released preferably has a vapor pressure lower than the predetermined pressure at which the sorbent material is sorptively saturated. The apparatus also includes means for selectively exposing the sorbent material to the atmosphere in order to allow the gaseous material to be desorptively released.

In a preferred form of the apparatus and method according to the present invention, the sorbent material is first depressurized to a pressure lower than the predetermined saturation pressure level prior to being sorptively saturated with the gaseous material. Preferably the sorbent material is heated during such depressurization in order to more effectively clear the sorbent material of undesirable sorbed contaminants or other substances, thereby increasing the sorptive storage capability of the sorbent material for the desired gaseous material to be released to the atmosphere.

Additional objects, advantages, and features of the present invention will become apparent from the following description and the appended claims, taken in conjunction with the accompanying drawings.

BRIEF DESCRIPTION OF THE DRAWINGS

FIG. 1 is an overall perspective view of an apparatus for releasing a gaseous material into the atmosphere in accordance with the present invention.

FIG. 2 is a cross-sectional view taken generally along line 2—2 of FIG. 1.

FIG. 3 is an overall perspective view of a sorbent material which has been sorptively saturated with the gaseous material to be released to the atmosphere and, which has been molded into a decorative shape.

FIG. 4 is a cross-sectional view of another application of the present invention, in which the invention is employed in an air supply system for controlled release of a gaseous material into an environmental space.

FIG. 5 is a diagrammatic representation of a preferred technique for loading the gaseous material onto the sorbent material.

DETAILED DESCRIPTION OF THE PREFERRED EMBODIMENTS

FIGS. 1 through 5 depict various exemplary embodiments of the present invention for purposes of illustration. One skilled in the art will readily recognize from the following discussion that the principles of the invention are equally applicable in devices and applications other than those illustratively shown in the drawings.

Referring to FIGS. 1 and 2, an air freshener 10 according to the present invention typically includes a base 12 and a top 14, with a number of tabs 16 protruding from the base 12 to slideably engage the top 14. When the top 14 is slideably moved away from the base 12, a number of openings 18 are provided therebetween in order to expose the interior of the air freshener 10 to the atmosphere.

Within the interior of the air freshener 10, a number of prongs 20, or other similar suitable structures, are provided for retaining a sorbent material 22 within the interior of the air freshener 10. The sorbent material 22 can take many forms, including a mesh or fabric type of material onto which a sorbent material has been affixed, or alternatively, the sorbent material can be formed and shaped into the desired configuration.

When the top 14 is moved away from the base 12 in order to form the openings 18, air from the atmosphere is free to flow through the interior of the air freshener 10, to contact the sorbent material 22. The sorbent material 22 has been previously sorptively saturated with a predetermined quantity of the gaseous material to be released into the atmosphere. Such gaseous material has been previously sorptively loaded onto the sorbent material 22 at a predetermined pressure, preferably approximately equal to atmospheric pressure. Because of the preferred low vapor pressure of the gaseous material to be released, small predetermined quantities of the gaseous material are released into the air flowing through the air freshener 10 in a controlled concentration and allowed to diffuse throughout the atmosphere. Because of the high storage capabilities of the sorbent material, which can be composed of an adsorbent material, such as activated carbon, ziolite, selica gel, or clay, for example, or which can alternatively be composed of an absorbent material, for useful life of the air freshener 10 is greatly increased over that of the previously-known air freshener devices described above.

The gaseous material, which is sorptively saturated onto the sorbent material 22, can be an odorant material in order to provide a pleasant scent in the atmosphere, or alternatively the material to be released can be an insect repellant in order to provide a relatively insect-free environment, or even an antiseptic or other medicinal material in order to provide a germ-free environment or to aid in other medical treatments.

In lieu of the air freshener apparatus 10 shown in FIGS. 1 and 2, the sorbent material can be shaped, molded, or otherwise formed into a solid shape such as the decorative sorbent material item 26 shown in FIG. 3. Such decorative item 26 can then be placed on a convenient surface in the region into which the gaseous material is to be released, or otherwise affixed to any convenient object in the area in accordance with various mounting or fastening techniques well-known to those skilled in the art.

FIG. 4 illustrates another exemplary application of the present invention, in which a building structure 30 includes a wall 32 having an opening 34 therein for receiving and housing an air supply grill or register 36. The air supply register 30 is connected in fluid communication with an air supply duct 38. Upstream of the air supply register 36, the supply duct 38 contains a sorbent material screen 40, or other suitable porous medium on to which the sorbent material is affixed, with the sorbent material screen 40 being placed in the air stream such that air from the air supply duct 38 flows through the sorbent material screen 40 and the air supply register 36 into the space 42.

The sorbent material screen 40 has been previously sorptively saturated with the gaseous material to be released into the space 42, in a manner such as that described above in connection with FIGS. 1 and 2. Thus, the present invention is usable to provide an apparatus and method to supply a pleasant scent to the space 42, for effecting a germ-free environment in the space 42, wherein the gaseous material to be released is an antiseptic, or alternatively, the gaseous material can be an insect repellant suitable for use in the space 42.

FIG. 5 diagrammatically illustrates a technique for preparing the sorbent material for use in accordance with the present invention. Although the sorbent material 22 on FIGS. 1 and 2 is diagrammatically repesented in FIG. 5, the principles depicted in FIG. 5 are equally applicable to any of the embodiments of the present inventions.

First, in the preferred form of the present invention, the sorbent material 22 is subjected to a reduced pressure level, preferably substantially below atmospheric pressure, as diagrammatically represented by the vacuum arrow 46 shown in FIG. 5. Preferably, during such depressurization, heat is added as is diagrammatically represented by the heat arrow 48, in order to release as much as possible of any undesired contaminants or other substances that had previously been sorbed by the sorbent material 22. Next, the desired gaseous material to be released into the atmosphere is introduced onto the sorbent material as diagrammatically represented by gas arrow 50 in FIG. 5, in order to sorptively saturate the sorbent material 22 with a desired gaseous material to be released. Preferably, such sorptive saturation is performed by introducing the gaseous material 50 under pressure in order to accomplish sorptive saturation at a predetermined pressure level, preferably approximately equal to atmospheric pressure.

The sorptively saturated sorbent material 22 is then selectively placed in communication with air in the atmosphere, such as in the air freshener 10 illustrated in FIGS. 1 and 2, for example, in order to allow the previously sorptively stored gaseous material to be released into the atmosphere. Such release occurs primarily because of the low vapor pressure of the gaseous material to be released, but can also occur as a result of a displacement of the gaseous material on the sorbent material 22 by other substances or materials in the atmosphere which are preferentially sorbed by the sorbent material 22. Because of the high-capacity storage capabilities of the adsorbent or absorbent material 22, the air freshener 10 or other apparatuses used in accordance with the present invention, are capable of providing an effective mechanism for releasing the gaseous material into the atmosphere in a simple, long-lived, and low-maintenance device.

The foregoing discussion discloses and describes exemplary embodiments of the present invention. One skilled in the art will readily recognize from such discussions, and from the accompanying drawings and claims, that various changes, modifications, and variations may be made therein without departing from the spirit and scope of the invention as defined in the following claims.

We claim:

1. A method of releasing a gaseous material into the atmosphere, said method comprising:
   providing a sorbent material;
   heating and depressurizing said sorbent material to a pressure lower than atmosphere pressure;
   sorptively saturating said depressurized sorbent material with a predetermined quantity of the gaseous material at approximately atmospheric pressure, the gaseous material having a vapor pressure lower than atmospheric pressure; and
   exposing said sorptively saturated sorbent material to the atmosphere in order to allow the gaseous material to be desorptively released to the atmosphere.

2. A method according to claim 1, wherein said sorbent material is an adsorbent material.

3. A method according to claim 2, wherein said adsorbent material includes an activated carbon.

4. A method according to claim 1, wherein said sorbent material is an absorbent material.

5. A method according to claim 1, wherein the gaseous material is an odorant.

6. A method according to claim 1, wherein the gaseous material is an insect repellant.

7. A method according to claim 1, wherein the gaseous material is an antiseptic.

8. A method according to claim 1, wherein the gaseous material is introduced onto said sorbent material in a gaseous state and sorptively saturated thereby.

9. A method according to claim 1, wherein the gaseous material is introduced onto said sorbent material in a liquid state, said vapor pressure being sufficiently low to allow at least a portion of said predetermined quantity of the gaseous material to be sorbed by the sorbent material in a gaseous state.

* * * * *